United States Patent [19]
Niemeyer et al.

[11] Patent Number: 5,843,059
[45] Date of Patent: Dec. 1, 1998

[54] ABSORBENT COMPOSITE AND DISPOSABLE ABSORBENT GARMENT COMPRISING SAME

[75] Inventors: Michael John Niemeyer, Appleton; Melissa Christine Putzer, Oshkosh, both of Wis.

[73] Assignee: Kimberly-Clark Worldwide, Inc., Neenah, Wis.

[21] Appl. No.: 559,385

[22] Filed: Nov. 15, 1995

[51] Int. Cl.⁶ .................................................. A61F 13/15
[52] U.S. Cl. ............................................ 604/368; 604/374
[58] Field of Search .................................. 604/358, 365, 604/367, 368, 374, 375, 378

[56] References Cited

U.S. PATENT DOCUMENTS

| | | | |
|---|---|---|---|
| 4,647,636 | 3/1987 | Makita et al. | 526/206 |
| 4,710,187 | 12/1987 | Boland et al. | 604/385 A |
| 4,758,617 | 7/1988 | Tanioku et al. | 524/413 |
| 4,762,521 | 8/1988 | Roessler et al. | 604/38 SA |
| 4,770,656 | 9/1988 | Proxmire et al. | 604/393 |
| 4,798,603 | 1/1989 | Meyer et al. | 604/378 |
| 5,147,343 | 9/1992 | Kellenberger | 604/372 |
| 5,149,335 | 9/1992 | Kellenberger | 604/372 |
| 5,219,653 | 6/1993 | Suga et al. | 428/332 |
| 5,364,382 | 11/1994 | Latimer et al. | 604/378 |
| 5,380,808 | 1/1995 | Sumiya et al. | 526/317.1 |
| 5,411,497 | 5/1995 | Tanzer et al. | 604/368 |
| 5,425,725 | 6/1995 | Tanzer et al. | 604/368 |
| 5,429,629 | 7/1995 | Latimer et al. | 604/378 |
| 5,433,715 | 7/1995 | Tanzer et al. | 604/368 |
| 5,509,915 | 4/1996 | Hanson et al. | 604/378 |
| 5,593,399 | 1/1997 | Tanzer et al. | 604/368 |

FOREIGN PATENT DOCUMENTS

| | | |
|---|---|---|
| 0 539 703 A1 | 5/1993 | European Pat. Off. ........ A61F 13/15 |
| 0 601 529 A1 | 6/1994 | European Pat. Off. . |
| 0 615 736 A1 | 9/1994 | European Pat. Off. . |

OTHER PUBLICATIONS

"Surface and Colloid Science" vol. II, pp. 31–90 Experimental Methods Good and Stromberg (Plenum Press 1979).
Sales Brochure Neo Curd Meter M302 with translation.
Gel Strength Test Method.
Draft Specifications for Aqua Keep SA–60S, Mar. 20, 1993.
U.S. Ser. No. 07/757,760 to William D. Hanson et al. entitled "Thin Absorbent Article Having Rapid Uptake Of Liquid" filed Sep. 11, 1991.
U.S. Ser. No. 08/096,654 to William D. Hanson et al. entitled "Thin Absorbent Article Having Rapid Uptake Of Liquid" filed Jul. 22, 1993.
U.S. Ser. No. 08/145,926 to R. W. Tanzer et al. entitled "Absorbent Article Which Includes Superabsorbent Material Located in Discreet, Elongate Pockets Placed In Selected Patterns" filed Oct. 29, 1993.

*Primary Examiner*—Mark O. Polutta
*Attorney, Agent, or Firm*—Brinks Hofer Gilson & Lione

[57] ABSTRACT

Disclosed is an absorbent composite suitable for use in disposable absorbent garments and an absorbent garment including such a composite. The composite includes a means for containing a superabsorbent material and a superabsorbent material contained by the containment means. The superabsorbent material has a Gel Integrity Index of at least about 1500 kilograms (force)×millimeters. Further, the superabsorbent material is present in the containment means in an amount of from about 10 to about 100 weight percent based on total weight of the containment means and the superabsorbent material.

71 Claims, 8 Drawing Sheets

ABSORBENT COMPOSITE AND DISPOSABLE ABSORBENT GARMENT COMPRISING SAME

BACKGROUND OF THE INVENTION

1. Field of the Invention

The present invention relates to absorbent composites comprising a superabsorbent material and to absorbent garments comprising such composites.

2. Description of the Related Art

Absorbent composites suitable for use in disposable absorbent garments such as diapers, adult incontinent products, feminine care products, training pants, and the like, are known. Generally, such absorbent composites comprise a means of containing a high-absorbency material and a high-absorbency material. Suitable means for containing the high-absorbency material include fibrous matrixes such as those formed from airlaid cellulose fibers or a coform material comprising cellulose fibers and meltblown polyolefin fibers. A wide variety of high-absorbency materials (also known as superabsorbent materials) are known to those skilled in the art.

Disposable absorbent garments formed from absorbent composites are intended to perform many uses. For example, disposable absorbent garments in the form of infant diapers are placed on children and are intended to absorb body fluids for a given period of time. During daytime use, care givers are generally readily available and will often change an infant's diaper after a single or perhaps two liquid insults. In contrast, the same diaper can be placed on an infant prior to the infant going to bed at night. This diaper may then stay on the infant until morning, a period of eight or more hours. This diaper will be subjected to three, four, or more liquid insults. Thus, a diaper intended for overnight use will have its absorbent ability taxed to a greater extent than a diaper intended for daytime use.

Similarly, cultural differences among different groups of people have been found to produce different diapering habits. That is, some cultural groups tend to change diapers more or less frequently than others. Thus, in certain cultures, even during daytime usage, a diaper may be subjected to three, four, or more liquid insults.

Unfortunately, diapers which perform completely satisfactory in circumstances where they are subjected to one or possibly two liquid insults can perform unsatisfactorily when subjected to three, four, or more liquid insults. This is, of course, undesirable.

It is possible to design diapers specific for daytime use and diapers specific for nighttime use. Unfortunately, this places a burden on the consumer to maintain proper supplies of both types of diapers. Moreover, it places the added burden on the consumer to time changing the diapers so that an overnight diaper is on the infant when the infant goes to sleep for the night. Such a solution to the described problem has been found generally unacceptable.

It is desirable to provide an absorbent composite which is capable of exhibiting excellent leakage performance in both low loading usage situations and high loading usage situations. It is to this goal that the present invention is directed.

SUMMARY OF THE INVENTION

In a first aspect, the present invention relates to an absorbent composite suitable for use in a disposable absorbent garment. The absorbent composite comprises means for containing a superabsorbent material and a superabsorbent material contained by said containment means. The superabsorbent material has a Gel Integrity Index, measuring the resistance to penetration of a gel slurry containing the superabsorbent material, of at least about 1500 kilogram (force)×millimeters ($Kg_f \times mm$). The superabsorbent material is present in the containment means in an amount of from about 10 to about 100 weight percent, based on the total weight of said containment means and said superabsorbent material. In one specific embodiment, the containment means comprises a fibrous matrix and the superabsorbent material is present in said fibrous matrix.

In a second aspect, the present invention relates to a disposable absorbent garment. The disposable absorbent garment comprises an outer cover, a bodyside liner superimposed on said outer cover, and an absorbent composite located between said outer cover and said bodyside liner. The absorbent composite comprises means for containing a superabsorbent material and a superabsorbent material contained by said containment means. The superabsorbent material has a Gel Integrity Index of at least about 1500 $Kg_f \times mm$. The superabsorbent material is present in said containment means in an amount of from about 10 to about 100 weight percent, based on the total weight of said containment means and said superabsorbent material. In one preferred embodiment, the containment means comprises a fibrous matrix and the superabsorbent material is present in said fibrous matrix.

DETAILED DESCRIPTION OF A PREFERRED EMBODIMENT

Figure 1:
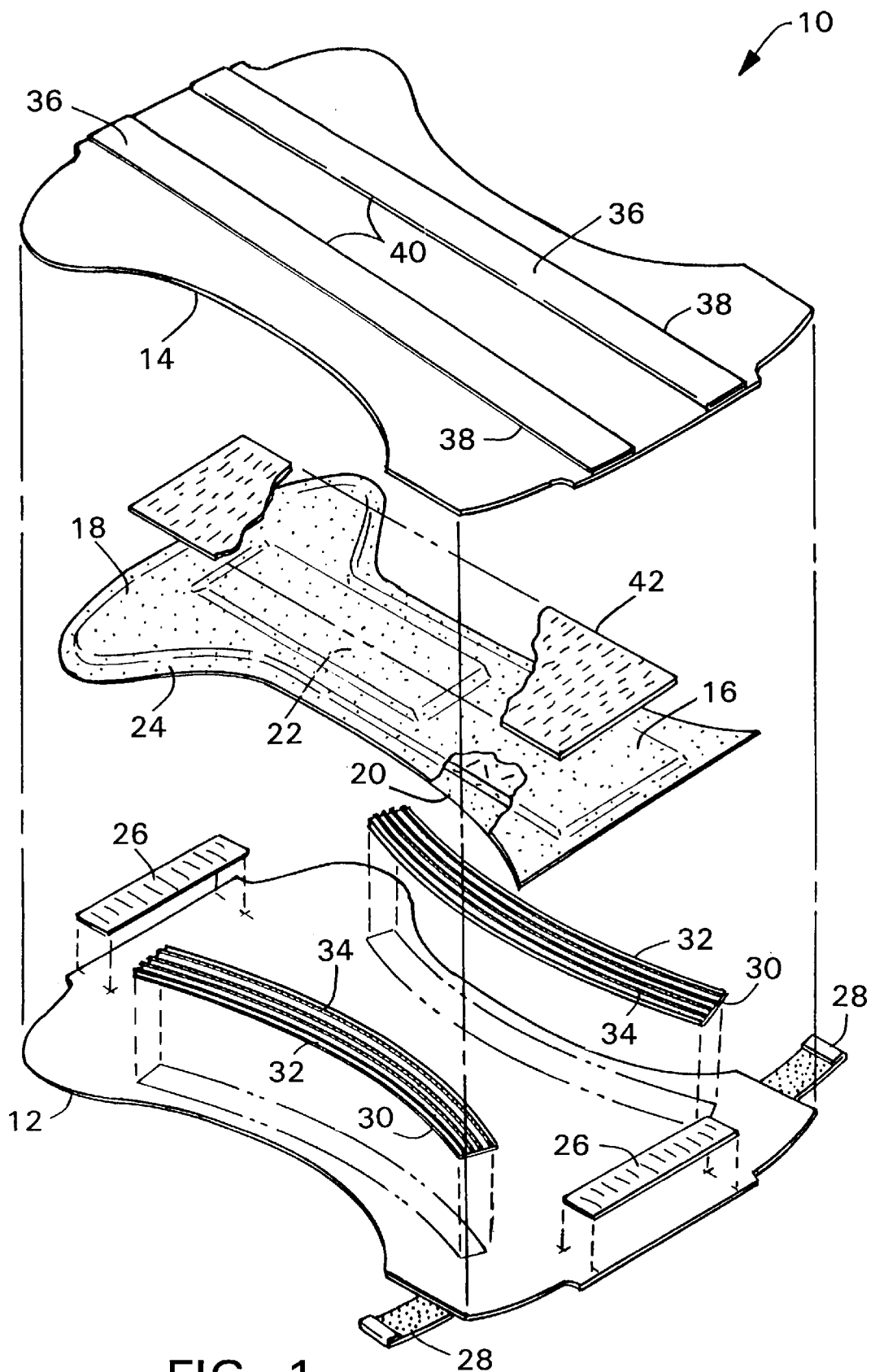
FIG. 1 illustrates an exploded perspective view of a diaper according to one embodiment of the present invention.

In one aspect, the present invention concerns absorbent composites and disposable absorbent garments possessing improved, desirable characteristics achieved by the careful selection and use of the superabsorbent material employed in forming such absorbent composites and disposable absorbent garments.

Specifically, in one aspect, the present invention concerns an absorbent composite comprising means for containing a superabsorbent material and a superabsorbent material contained by said containment means. In a specific embodiment, the present invention concerns an absorbent composite comprising a fibrous matrix and a superabsorbent material present in said fibrous matrix.

As used herein, the term "superabsorbent material" refers to a water-swellable, water-insoluble organic or inorganic material capable, under the most favorable conditions, of absorbing at least about 20 times its weight and, preferably, at least about 30 times its weight in an aqueous solution containing 0.9 weight percent of sodium chloride. Organic materials suitable for use as a superabsorbent material of the present invention can include natural materials such as agar, pectin, guar gum, and the like, as well as synthetic materials such as synthetic hydrogel polymers. Such hydrogel polymers include, for example, alkali metal salts of polyacrylic acids, polyacrylamides, polyvinyl alcohol, ethylene maleic anhydride copolymers, polyvinyl ethers, hydroxypropyl cellulose, polyvinylmorpholinone, and polymers and copolymers of vinyl sulfonic acid, polyacrylates, polyacrylamides, polyvinyl pyridines, and the like. Other suitable polymers include hydrolyzed acrylonitrile grafted starch, acrylic acid grafted starch, and isobutylene maleic anhydride copolymers and mixtures thereof. The hydrogel polymers are preferably lightly crosslinked to render the material substantially water insoluble. Crosslinking may, for example, be by irradiation, or by covalent, ionic, Van der Waals, or hydrogen bonding. Preferred superabsorbent materials are shell crosslinked so that the outer surface or shell of the superabsorbent particle, fiber, flake, sphere, etc. possesses a higher crosslink density than the inner portion of the superabsorbent. The superabsorbent materials may be in any form suitable for use in absorbent composites including particles, fibers, flakes, spheres, and the like. In one preferred embodiment of the present invention, the superabsorbent material comprises particles of hydrocolloids, preferably an ionic hydrocolloid.

While a wide variety of superabsorbent materials are known, the present invention relates, in one aspect, to the proper selection of a superabsorbent material to allow formation of improved absorbent composites and disposable absorbent garments.

Applicants have discovered that the performance of a superabsorbent material in absorbent composites intended for overnight usage or other usage situations, in which the absorbent composites will be subjected to high levels of liquid loading, depends, at least in part, on the gel characteristics of the superabsorbent material contained in the composite. As used herein, the gel characteristics of a superabsorbent material refers to the Gel Integrity Index herein described in greater detail in connection with the examples. Stated generally, the Gel Integrity Index is a measure of the resistance to flow as measured by penetration resistance of the gel slurry formed when the superabsorbent material is subjected to a high level of liquid loading.

Specifically, the Gel Integrity Index measures the resistance to penetration of the gel slurry formed by allowing a superabsorbent material to free swell in an aqueous solution containing 0.9 weight percent sodium chloride in which the superabsorbent material and sodium chloride solution are present in a weight ratio of 1:50, respectively. Briefly stated, the Gel Integrity Index is measured by (1) mixing one part by weight of superabsorbent material having a moisture content of less than 10 weight percent and 50 parts of an aqueous solution containing 0.9 weight percent sodium chloride, in a container having a 33 millimeter diameter and a height of 62 millimeters;

(2) allowing the superabsorbent material to swell for at least one hour until it appears to have generally reached equilibrium; and (3) measuring the resistance of a sample of the mixture of swollen superabsorbent and aqueous solution of sodium chloride to penetration to a test probe, by (a) attaching a clear anodized aluminum test probe having a 1.27 centimeter diameter, a length of 11.43 centimeters, and a rounded end having a 6.35 millimeter radius, to descend downward from a load cell capable of determining the load exerted on the load cell by the test probe;

(b) raising the sample of the mixture of swollen superabsorbent and aqueous solution of sodium chloride to the rounded end of the probe until a load greater than 0.1 gram but less than one gram is exerted on the load cell;

(c) lowering the test probe into the sample, for a distance of 40 millimeters at a constant speed of 16 inches per minute; and (d) determining the resistance of the sample to the introduction of the test probe into the sample, as the probe penetrates from 15 to 40 millimeters into the sample. If the superabsorbent is in particulate form, the particles should preferably be screened to have a maximum cross-sectional diameter within the range of from about 50 microns to about 1000 microns, more preferably from about 100 microns to about 800 microns.

Superabsorbent materials suitable for use in the present invention have a Gel Integrity Index of at least about 1500 $Kg_f \times mm$, alternatively of at least about 1600 $Kg_f \times mm$, alternatively of at least about 1700 $Kg_f \times mm$, alternatively of at least about 1900 $Kg_f \times mm$, alternatively of at least about 2100 $Kg_f \times mm$. In specific embodiments, the superabsorbent materials suitable for use in the present invention have a Gel Integrity Index of from about 1500 $Kg_f \times mm$ to about 5000 $Kg_f \times mm$, alternatively of from about 1900 $Kg_f \times mm$ to about 5000 $Kg_f \times mm$, still further alternatively from about 1700 $Kg_f \times mm$ to about 4500 $Kg_f \times mm$.

Applicants have discovered that superabsorbent materials, possessing a Gel Integrity Index as described above, are capable of producing absorbent composites and disposable absorbent garments comprising such composites which are particularly well suited for both daytime (low liquid loadings) and overnight (high liquid loadings) usage, or for daytime usages where the absorbent composites will be subjected to a high level of liquid loadings. Such high levels of liquid loadings can result from the period of time the disposable absorbent garment is in use on a wearer or from the particular physical characteristics of the wearer.

Exemplary of specific superabsorbent materials suitable for use in the present invention are polyacrylate materials obtained from Allied-Colloids under the designation DP6-6664, Batch 1, 2, 4, 11, and 12.

In one preferred embodiment of the present invention, the superabsorbent material is in the form of particles which, in the unswollen state, have a maximum cross-sectional diameter within the range of from about 50 microns to about 1000 microns, preferably within the range of from about 100 microns to about 800 microns, as determined by sieve analysis according to American Society for Testing and Materials (ASTM) test method D-1921. It is understood that particles of superabsorbent material falling within the ranges described above may comprise solid particles, porous particles, or may be agglomerated particles comprising many smaller particles agglomerated into particles within the described size ranges.

In addition to the superabsorbent materials described above, the absorbent composites according to the present invention comprise means to contain the superabsorbent material. Any means capable of containing the described superabsorbent materials, which means is further capable of being located in a disposable absorbent garment, is suitable for use in the present invention. Many such containment means are known to those skilled in the art. For example, the containment means may comprise a fibrous matrix such as an airlaid or wet-laid web of cellulosic fibers, a meltblown web of synthetic polymeric fibers, a spunbonded web of synthetic polymeric fibers, a coformed matrix comprising cellulosic fibers and fibers formed from the synthetic polymer material, airlaid, heat-fused webs of synthetic polymeric materials, open-celled foams, and the like.

Alternatively, the containment means may comprise two layers of material which are joined together to form a pocket or compartment, more particularly, a plurality of pockets, which pockets contain a superabsorbent material. In such a case, at least one of the layers of material should be water pervious. The second layer of material may be water pervious or water impervious. The layers of material may be clothlike woven or nonwovens, closed- or open-celled foams, perforated films, elastomeric materials, or may be fibrous webs of material. When the containment means comprises layers of material, the material should have a pore structure small enough or tortuous enough to contain the majority of superabsorbent material. The containment means may also comprise a laminate of two layers of material between which the superabsorbent material is located and contained.

Further, the containment means may comprise a support structure, such as a polymeric film, on which the superabsorbent material is affixed. The superabsorbent material may be affixed to one or both sides of the support structure which may be water pervious or water impervious.

The superabsorbent material is present in the containment means in an amount of from about 10 to about 100 weight percent, alternatively of from about 30 to about 100 weight percent, alternatively of from about 50 to about 100 weight percent, alternatively of from about 30 to about 70 weight percent based on total weight of said containment means and said superabsorbent material.

In one specific embodiment, the containment means comprises a matrix of fibers. The superabsorbent material is mixed with the fibers of the matrix to form a mixture. The superabsorbent material is present in the mixture of fibers and superabsorbent materials in an amount of from about 10 to about 100 weight percent, alternatively of from about 30 to about 100 weight percent, alternatively of from about 50 to about 100 weight percent, alternatively of from about 30 to about 70 weight percent, based on the total weight of the matrix of fibers and said superabsorbent material. Any fibers capable of forming a containment means capable of containing a superabsorbent material and of forming a composite when in combination with the superabsorbent material are believed suitable for use in the present invention. It is often preferred that the fibers are hydrophilic. As used herein, a fiber will be considered to be "hydrophilic" when it possesses a contact angle of water in air of less than 90 degrees. For the purposes of this application, contact angle measurements are determined as set forth by Good and Stromberg in "Surface and Colloid Science," Volume 11 (Plenum Press, 1979).

Fibers suitable for use in the present invention include cellulosic fibers such as wood pulp fluff, cotton, cotton linters, rayon, cellulose acetate, and the like, as well as synthetic polymeric fibers. The synthetic polymeric fibers may be formed from inherently hydrophilic polymeric materials or may be formed from inherently hydrophobic polymeric materials (water in air contact angle of greater than 90 degrees), which fibers are then treated to render at least the outer surface of the fibers hydrophilic. For example, hydrophilic fibers may be formed from an intrinsically hydrophilic polymer such as a block copolymer of nylon, e.g., nylon-6, and a polyethylene oxide diamine. Such block copolymers are commercially available from Allied Signal Inc. under the trade designation HYDROFIL™. Alternatively, the fibers may be formed from an intrinsically hydrophobic polymer such as polyolefin or polyester which has been surface modified to provide a generally nonfugitive hydrophilic surface.

When the hydrophilic fibers are formed by applying a hydrophilic surface treatment to a generally hydrophobic polymer, it is believed desirable to employ a generally nonfugitive surface treatment in order to obtain the desired performance standards. Absorbent structures employed in absorbent garments such as diapers are, as discussed above, often subjected to multiple liquid insults. If the surface treatment is fugitive, it may be washed off with the initial insult, thus, exposing the hydrophobic fiber surface. The hydrophobic fiber surface may impede the absorption performance of the absorbent structure. Of course, there are instances where hydrophobic fibers may be employed depending in part on the fluid to be absorbed.

The synthetic polymeric fibers suitable for use in the present invention may suitably be formed through a melt-extrusion process wherein fibers of a polymeric material are extruded and attenuated to produce fibers having a desired diameter. Alternatively the fibers may be formed through a spinning process. Any fiber-producing process known to those skilled in the art is believed to be suitable for use in the present invention.

Fibers suitable for use in the present invention generally have a length of at least about 1 millimeter. The fibers may have a maximum length approaching infinity. That is to say, the fibers may be essentially continuous, such as those fibers formed through a meltblowing process under certain conditions known to those skilled in the art.

Reference to a "mixture" is intended to refer to a combination of fibers and superabsorbent material in which the superabsorbent material is in direct contact with the fibers or is not substantially prevented from migrating into contact with the fibers. Thus, for example, in a multi-layered absorbent core in which the first layer comprises an airlaid mixture of wood pulp fluff and superabsorbent material and the second layer comprises only airlaid fluff, only the first layer is considered a "mixture" provided substantial dry migration of the superabsorbent material between the two layers is prevented. Methods of preventing such migration are known and include separating the layers by a tissue wrapsheet, high density fiber layer, or similar means to prevent substantial dry migration of the superabsorbent material between the two layers. The mixture of superabsorbent materials and fibers may be relatively homogenous or relatively nonhomogeneous. In the case of a nonhomogeneous mixture, the superabsorbent may be arranged in a gradient or may be layered with the fibers.

When the containment means comprises a mixture of fibers and a superabsorbent material, the mixture of fibers and the superabsorbent material may be formed in a wide variety of ways. For example, the mixture may be formed by air laying or wet laying the fibers in the superabsorbent material, according to processes known in the art, to form batts of the mixture. Air laying the mixture of fibers and superabsorbent material is intended to encompass both the situation wherein preformed fibers are air laid with the superabsorbent material as well as the situation in which the superabsorbent material is mixed with the fibers as the fibers are being formed, such as through a meltblowing process.

In one preferred embodiment of the present invention in which the superabsorbent material is employed in a relatively high concentration, 30 weight percent or greater, the absorbent composites according to the present invention may have an average thickness of less than about 0.5 inch (12.7 millimeters), particularly of less than about 0.3 inch (7.6 millimeters), and more particularly, of less than about 0.15 inch (3.8 millimeters).

As used herein, reference to the average thickness of an absorbent composite is intended to refer to the average of a number of thickness measurements taken under an applied load of about 0.2 pound per square inch. The number of thickness measurements taken is sufficient to represent the average thickness of the entire absorbent composite.

The absorbent composites of the present invention generally have an average basis weight of from about 50 to about 1000 grams per square meter, particularly of from about 100 to about 900 grams per square meter. The average basis weight of an absorbent composite can be determined by weighing the absorbent composite, determining the surface area of the major planar surface of the absorbent composite and converting to standard units such as grams per square meter.

The absorbent composites according to the present invention are suited to absorb many fluids, including body fluids such as urine, menses, and blood; and are suited for use in absorbent garments such as diapers, adult incontinent products, bed pads, and the like; in catamenial devices such as sanitary napkins, tampons, and the like; and in other absorbent products such as wipes, bibs, wound dressings, food packaging and the like. Accordingly, in another aspect, the present invention relates to a disposable absorbent garment comprising an absorbent composite as described above. A wide variety of absorbent garments are known to those skilled in the art. The absorbent composites of the present invention can be incorporated into such known absorbent garments. Exemplary absorbent garments are generally described in U.S. Pat. Nos. 4,710,187 issued Dec. 1, 1987, to Boland et al.; 4,762,521 issued Aug. 9, 1988, to Roessler et al.; 4,770,656 issued Sep. 13, 1988, to Proxmire et al.; 4,798,603 issued Jan. 17, 1989, to Meyer et al.; 5,411,497 issued May 2, 1995 to Tanzer et al.; 5,433,715 issued Jul. 18, 1995 to Tanzer et al.; 5,425,725 issued Jun. 20, 1995 to Tanzer et al.; and commonly assigned U.S. patent application Ser. No. 08/096,654, now U.S. Pat. No. 5,509,915 filed Jul. 22, 1993, as a continuation of Ser. No. 07/757,760, filed Sep. 11, 1991, and now abandoned in the name of Hanson et al. (EP 0 539 703) and Ser. No. 08/369,558 now U.S. Pat. No. 5,593,399 filed Jan. 6, 1995, as a continuation of Ser. No. 145,926, filed Oct. 29, 1993 in the name of Tanzer et al., all of which are incorporated herein by reference. As a general rule, the absorbent disposable garments according to the present invention comprise a bodyside liner adapted to contact the skin of a wearer, an outer cover superimposed in facing relation with said liner, and an absorbent composite, such as those described above, superimposed on said outer cover and located between the bodyside liner and the outer cover. Those skilled in the art will recognize materials suitable for use as the bodyside liner and outer cover. Examples of materials suitable for use as the bodyside liner are hydrophilized spunbond polypropylene or polyethylene with a basis weight of from about 15 to about 25 grams per square meter, and the like. Examples of materials suitable for use as the outer cover are water-impervious materials such as polyolefin films, as well as water-pervious or water vapor-pervious materials.

Turning now to the drawings, FIG. 1 illustrates an exploded perspective view of a disposable diaper according to one embodiment of the present invention. Disposable diaper 10 includes an outer cover 12, a bodyside liner 14, and an absorbent composite 16 between the bodyside liner 14 and the outer cover 12. The absorbent composite 16 comprises an airlaid mixture of wood pulp fibers and superabsorbent material. The absorbent composite is surrounded by a two-piece wrapsheet comprising upper wrapsheet layer 18 and lower wrapsheet layer 20. The absorbent composite 16 has a profiled thickness to define an area 22 of increased basis weight. The two-piece wrapsheet extends beyond the edges of the absorbent composite 16 to define perimeter 24 which can be sealed to prevent superabsorbent material from migrating out of the diaper.

Attached to outer cover 12 are waist elastics 26, fastening tapes 28, and leg elastics 30. The leg elastics 30 comprise a carrier sheet 32 and individual elastic strands 34.

The bodyside liner 14 includes containment flaps 36 having proximal edges 38 and distal edges 40. A surge management material 42 is located between the bodyside liner 14 and the upper wrapsheet layer 18 associated with absorbent composite 16.

The exact construction method and materials of the diaper illustrated in FIG. 1 is set forth in greater detail in commonly assigned U.S. patent application Ser. No. 08/096,654, filed Jul. 22, 1993, in the name of Hanson et al., U.S. Pat. No. 5,509,915 previously incorporated herein by reference. Possible modifications to the diaper illustrated in FIG. 1 are set forth in commonly assigned U.S. Pat. Nos. 5,364,382 issued Nov. 15, 1994, to Latimer et al., and 5,429,629 issued Jul. 4, 1995 to Latimer et al. Such possible modifications include positioning the surge management layer 42 between the proximal edges 38 of the containment flaps 36 and reducing the length of the surge management layer to extend the length of the absorbent composite or massing (reduced length and increased basis weight) of the surge management layer in the area of the diaper where liquid waste initially accumulates (target zone).

Test Methods

Moisture Content of Superabsorbent Material

The following test method is suitably used to determine the moisture content of superabsorbent material.

Equipment Used:
1. An electronic balance accurate to 0.001 gram, such as that available from Sartorius Co. under the trade designation BP310S.
2. A forced-air oven capable of maintaining an internal temperature of 105° C.±2° C. Such an oven is commercially available from Blue M under the designation Stabil-Therm.
3. A desiccator containing fresh calcium chloride. Such a desiccator can be obtained from Baxter Scientific Co. under the designation Pyrex Knob Top Desiccator.
4. A 60 millimeter aluminum weighing dish, such as that available from Sargent Welch Co. under the designation #S 25725.

Test Procedure
1. Preheat oven to 105° C.±2° C.
2. Weigh the aluminum weighing dish and record the weight as W1.
3. Place 8–10 grams of superabsorbent material in the weighing dish.
4. Weigh the weighing dish and superabsorbent material and record the weight as W2.
5. Place the weighing dish and superabsorbent material in the preheated oven for 3 hours.
6. Remove the weighing dish and superabsorbent material from the oven and place in desiccator. Allow to cool for approximately 30 minutes.

7. Remove the weighing dish and superabsorbent material from the desiccator and immediately weigh the cooled weighing dish and superabsorbent material. Record the weight as W3.
8. The percent moisture is calculated by the formula:

% moisture=100×(W2−W3)/(W2−W1)

Gel Integrity Index

Equipment Used

Figure 2:
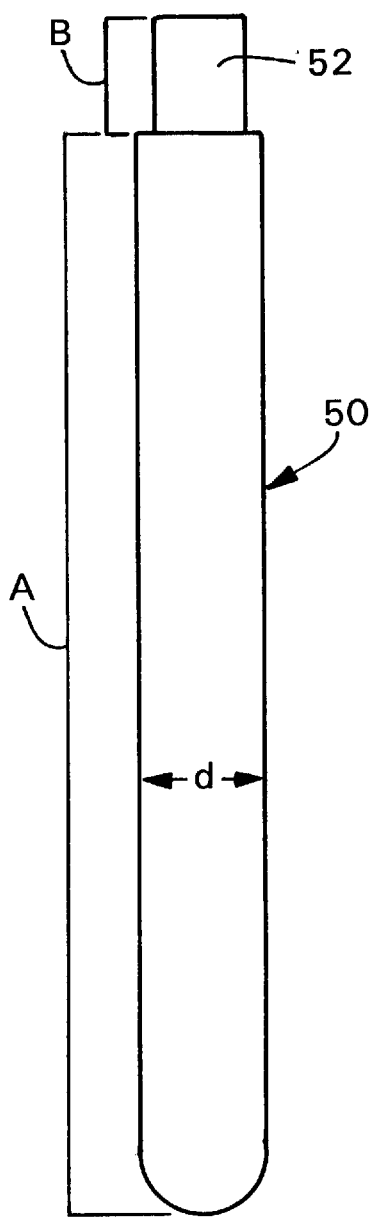
FIG. 2 illustrates the test probe used in conducting the Gel Integrity Index test described in connection with the examples.

1. An electronic balance accurate to 0.001 gram, such as that available from Sartorius Co. under the trade designation BP310S.
2. U.S. Standard 30 mesh and 50 mesh screens, automatic sieve shaker, such as a Ro-Tap Sieve Shaker commercially available from Baxter Scientific.
3. Air tight glass containers, such as those available from Baxter Scientific under the trade designation Qorpak Bottles AP-2103.
4. 0.87 percent aqueous saline solution commercially available from Baxter Scientific under the trade designation Blood Bank Saline.
5. A 33 millimeter diameter by 62 millimeter high, 55 milliliter capacity polystyrene vial, such as that commercially available from Baxter Scientific under the trade designation Continental Glass and Plastic Co. Polystyrene Snap Cap Vial.
6. A Tensile Tester, such as that commercially available from Instron under the trade designation Model #1122. The Tensile Tester is interfaced with a personal computer including Windows™ and Test Works™ for Windows software.
7. A 2000 gram compression load cell for the Tensile Tester of No. 6, which load cell is commercially available from Instron.
8. Test Works™ software commercially available from Sintech under the trade designation Test Works for Windows.
9. A 1.27 centimeter diameter (d) clear anodized aluminum test probe as illustrated in FIG. 2. With reference to FIG. 2, the test probe 50 has a length A of 11.43 centimeters. The test probe 50 has a threaded portion 52 having a length B of 1 centimeter. The threaded portion 52 is adapted to screw into the load cell of number 7 above. The end of probe 50 opposite threaded portion 52 is rounded (0.635 centimeter radius).
10. A laboratory jack
11. Polystyrene weigh boat, commercially available from Baxter Scientific under the trade designation S/P Brand dispo Weigh Boat Containers.

Sample Preparation

1. Take a quantity of superabsorbent material as it is received from the superabsorbent supplier, but having a moisture content of less than 10 weight percent, and prescreen according to ASTM Test Method D-1921. If the superabsorbent material has a moisture content of greater than 10 weight percent, it should be dried at about 105° C. until it has a moisture content of less than 10 weight percent. Fibrous superabsorbent materials do not need to be prescreened but should have (or be dried to) a moisture content of less than 10 weight percent. Transfer the superabsorbent material passing through the U.S. Standard 30 mesh screen and retained on the U.S. Standard 50 mesh screen (300–600 micron portion) of the superabsorbent material into the air tight container to prevent moisture pick-up.
2. Transfer 40 milliliters (+0.01 milliliter) of the 0.87 percent Baxter Blood Bank saline into the polystyrene vial.
3. Measure 0.80 gram of the superabsorbent material obtained under No. 1 above (300–600 micron particle size) into the polystyrene weigh boat. Transfer the superabsorbent material from the weigh boat into the polystyrene vial, place the cap on the vial, and swirl gently for 10 seconds. After swirling, allow the superabsorbent material to swell undisturbed at room temperature for one to eight hours. The superabsorbent is allowed to swell until it appears to have generally reached equilibrium (has stopped swelling). One hour is generally sufficient to reach this apparent equilibrium stage. Transfer the vial with as little movement as possible to the platform of the tensile tester. Triplicate samples for each superabsorbent material to be tested are prepared.

Test Set-Up

1. Plug the 2000 gram compression load cell into the tensile tester and allow it to warm up for at least 30 minutes.
2. Turn on the personal computer and enter the Windows™ program.
3. Enter the Testworks™ software.
4. Set the following parameters in the compression master preset program:

|   |   |   | Calculation Inputs |   |   |
|---|---|---|---|---|---|
| # | Label | Units | Default | Attribute | Panel Input |
| 0 | Gauge Length | mm | 75.00 | Display |  |
| 1 | Bonded Gage | In/In | 1.00 | HIDDEN | N |
| 2 | Removal Point | In | 1.00 | HIDDEN | N |
| 3 | Brk % Drop | % | 100.0 | HIDDEN | N |
| 4 | Brk Drop Elong | In | 0.001 | HIDDEN | N |
| 5 | Brk Load Value | Lb | 50.00 | HIDDEN | N |
| 6 | Yield Angie | deg | 0.00 | HIDDEN | N |
| 7 | Yield % SegLen | % | 10.00 | HIDDEN | N |
| 8 | Slope Tol. | % | 98.00 | HIDDEN | N |
| 9 | Slope % SegLen | % | 10.00 | HIDDEN | N |
| 10 | Min Slope Load | Lb | 0.00 | HIDDEN | N |
| 11 | Max Slope Load | Lb | 10000.00 | HIDDEN | N |
| 12 | Slope Min Strss | PSI | 0.00 | HIDDEN | N |
| 13 | Slope Max Strss | PSI | 1000.00 | HIDDEN | N |

-continued

| | | | | | |
|---|---|---|---|---|---|
| 14 | % Strain Point1 | % | 29.160 | OPTIONAL | N |
| 15 | % Strain Point2 | % | 5.00 | HIDDEN | N |
| 16 | START | mm | 15 | DISPLAY | N |
| 17 | END | mm | 40.00 | DISPLAY | N |
| 18 | Stress Point1 | PSI | 100.0 | HIDDEN | N |
| 19 | Stress Point2 | PSI | 200.0 | HIDDEN | N |
| 20 | Yield Offset | % | 2 | HIDDEN | N |
| 21 | Slack Pre–Load | Gm | 5.00 | OPTIONAL | N |
| 22 | % Strain Point3 | % | 2.92 | OPTIONAL | N |

Test Inputs

| # | Label | Units | Default | Attribute | Panel Input |
|---|---|---|---|---|---|
| 0 | Initial Speed | In/Min | 16.00 | HIDDEN | N |
| 1 | Speed | In/Min | 16.00 | OPTIONAL | N |
| 2 | % Strain Limit | % | 100.0 | HIDDEN | N |
| 3 | Deformation Lim | % | 52.00 | OPTIONAL | N |
| 4 | Load Limit HI | Gm | 2000 | OPTIONAL | N |
| 5 | Load Limit LO | Lb | −5000 | HIDDEN | N |
| 6 | Ext Limit HI | In | 3.000 | OPTIONAL | N |
| 7 | Ext Limit LO | In | −20.0 | HIDDEN | N |
| 8 | Strain Limit HI | % | 3000000.1 | HIDDEN | N |
| 9 | Strain Limit LO | % | −300000.0 | HIDDEN | N |
| 10 | Stress Limit HI | PSI | 2999999.9 | HIDDEN | N |
| 11 | Stress Limit LO | PSI | −3000000 | HIDDEN | N |
| 12 | #Cycles | (none) | 20.0 | HIDDEN | N |
| 13 | Time Limit | Sec | 10000 | HIDDEN | N |
| 14 | Brk Sensitivity | % | 110 | OPTIONAL | N |
| 15 | RETURN Point | In | 0.0 | HIDDEN | N |

Required Markers

| # | Category | Code | Attribute |
|---|---|---|---|
| 1 | BREAK POINT | F | HIDDEN |
| 2 | YIELD POINT | Y | HIDDEN |
| 3 | MODULOUS BEGIN | B | HIDDEN |
| 4 | MODULUS END | M | HIDDEN |

Optional Markers

| # | Category | Code | Attribute | Formula | Inputs |
|---|---|---|---|---|---|
| 5 | AT MIDPOINT | 0 | HIDDEN | | |
| 6 | AT PIP | 1 | HIDDEN | | |
| 7 | AT PIP | 2 | HIDDEN | | |
| 8 | AT PIP | 3 | HIDDEN | | |
| 9 | AT PIP | 4 | HIDDEN | | |
| 10 | FREE | B | FIXED | @INDEX(EXT,C16) | |
| 11 | FREE | E | FIXED | @INDEX(EXT,C17) | |
| 12 | FREE | 7 | HIDDEN | @INDEX(LOAD,PEAK) | |
| 13 | FREE | 8 | HIDDEN | @INDEX(LOAD,PEAK) | |
| 14 | FREE | 9 | HIDDEN | @INDEX(LOAD,PEAK) | |

Required Calculations

| # | Category | Procedure | Inputs |
|---|---|---|---|
| 0 | AREA | INACTIVE | |
| 1 | STRESS | 1/AREA | |
| 2 | Primary Strain | 1/100 | |
| 3 | Secondary Strain | 1/100 | |
| 4 | Break | INACTIVE | |
| 5 | Yield Point | INACTIVE | |
| 6 | Primary Slope | INACTIVE | |
| 7 | Slack Compensation | INACTIVE | |
| 8 | Offset Yield | INACTIVE | |
| 9 | Gauge Length Adjustment | INACTIVE | |

Sample Naming Format

| | | |
|---|---|---|
| Alias | Sample ID | Length = 30 |
| Alias | | Length = 0 |
| Alias | | Length = 0 |
| Alias | | Length = 0 |
| Alias | | Length = 0 |

-continued

Channel Mapping

| # | Label | Units Class | Status | Formula |
|---|---|---|---|---|
| [0] | EXTENSION | DIMENSION | ACTIVE | P0 |
| [1] | TIME | TIME | ACTIVE | P1 |
| [2] | LOAD | LOAD | ACTIVE | P2 |
| [3] | LOGICAL 3 | DIMENSION | INACTIVE | P3 |
| [4] | LOGICAL 4 | LOAD | INACTIVE | P4 |

Display Units

| | |
|---|---|
| Load | Gm |
| Extension | In |
| Speed | In/Min |
| Area | Sq.In. |
| Strain | % |
| Time | Min |
| Stress | PSI |

Specimen Inputs

| # | Label | Units | Default | Attribute | Panel Input |
|---|---|---|---|---|---|
| 0 | Diameter | In | 0.500 | HIDDEN | N |
| 1 | Length | In | 0.125 | HIDDEN | N |
| 2 | Height | In | 2.00 | HIDDEN | N |
| 3 | Area | Sq.In. | 2.00 | HIDDEN | N |
| 4 | Misc.Input 1 | (none) | 1.00 | HIDDEN | N |
| 5 | Misc.Input 2 | (none) | 1.00 | HIDDEN | N |
| 6 | Misc.Input 3 | (none) | 1.00 | HIDDEN | N |
| 7 | Misc.Input 4 | (none) | 1.00 | HIDDEN | N |

| | |
|---|---|
| Gage Removal | [N] |
| Pause for Gage Removal | [N] |

Reference Name:

| | |
|---|---|
| Reference Loaded | None |

Configuration

| | |
|---|---|
| Load Direction | UP |
| Extension Direction | UP |
| Compliance | No |
| End Of Test Action | GOTO |
| Method Type | STANDARD |

Move Segments

| | |
|---|---|
| Type | RESET EXTENSION |
| Status | ENABLE |
| Direction | NO CHANGE |
| Acquisition | INACTIVE |
| Data Points | 0 |
| End Action | CONTINUE |
| Message | |

Move Segments

| | |
|---|---|
| Type | TARE STRAIN 1 |
| Status | DISABLE |
| Direction | NO CHANGE |
| Aquisition | INACTIVE |
| Data Points | 0 |
| End Action | CONTINUE |
| Message | |
| Type | TARE STRAIN 2 |
| Status | DISABLE |
| Direction | NO CHANGE |
| Aquisition | INACTIVE |
| Data Points | 0 |
| End Action | CONTINUE |
| Message | |
| Type | GO TO STRAIN @ CONSTANT SPEED |
| Status | DISABLE |
| Direction | NO CHANGE |
| Aquisition | ACTIVE |
| Data Points | 500 |
| End Action | CONTINUE |

-continued

| | | Initial Speed to %strain point |
|---|---|---|
| Message | | |
| Type | | GO TO STRAIN @ CONSTANT SPEED |
| Status | | ENABLE |
| Direction | | DOWN (Testing Below The Crosshead) |
| Aquisition | | ACTIVE |
| Data Points | | 500 |
| End Action | | STOP |
| Message | | |

Sample Inputs

| # | Label | Default | Attribute |
|---|---|---|---|
| 0 | User Input 1 | User Default 1 | HIDDEN |
| 1 | User Input 2 | User Default 2 | HIDDEN |
| 2 | User Input 3 | User Default 3 | HIDDEN |
| 3 | User Input 4 | User Default 5 | OPTIONAL |
| 4 | User Input 5 | User Default 6 | HIDDEN |
| 5 | User Input 6 | User Default 6 | HIDDEN |
| 6 | User Input 7 | User Default 7 | HIDDEN |
| 7 | User Input 8 | User Default 8 | HIDDEN |
| 8 | User Input 9 | User Default 9 | HIDDEN |
| 9 | User Input 10 | User Default 10 | HIDDEN |

5. Calibrate the load cell to within 1 percent according to the calibration procedure supplied with the Tensile Tester.
6. Once calibrated, mount the load cell to the Tensile Tester frame and attach the 1.27 centimeter diameter test probe to the load cell.

Test Procedure

1. Click on "sample" at the top of the screen and type in a sample description. Press enter.
2. Zero the load on the load cell.
3. Remove the cap from one of the polystyrene vials containing the swollen superabsorbent material prepared as described above and place it on a laboratory jack located below the test probe which has been securely screwed into the load cell.
4. Raise the sample with the laboratory jack until a load greater than 0.1 gram but less than 1 gram is exerted on the load cell.
5. Re-zero the load on the load cell and then click on "run" at the top of the screen.
6. The Instron machine will then lower the 1.27 centimeter diameter test probe into the sample for a distance of 40 millimeters at a constant speed of 16 inches per minute.
7. When the probe stops, press "return" on the Instron panel and raise the probe from the sample. Wipe off the probe. Test the remaining two samples of the same material in the manner described above.

Print the results of the testing. The Gel Integrity Index is the area under the curve generated by the Tensile Tester equipment from initiation of the test procedure to the end of the procedure for the three test samples. The value is reported as the average energy of the three replications in kilogram (force)×millimeters.

Fluid Intake Evaluation

Figures 3, 4:
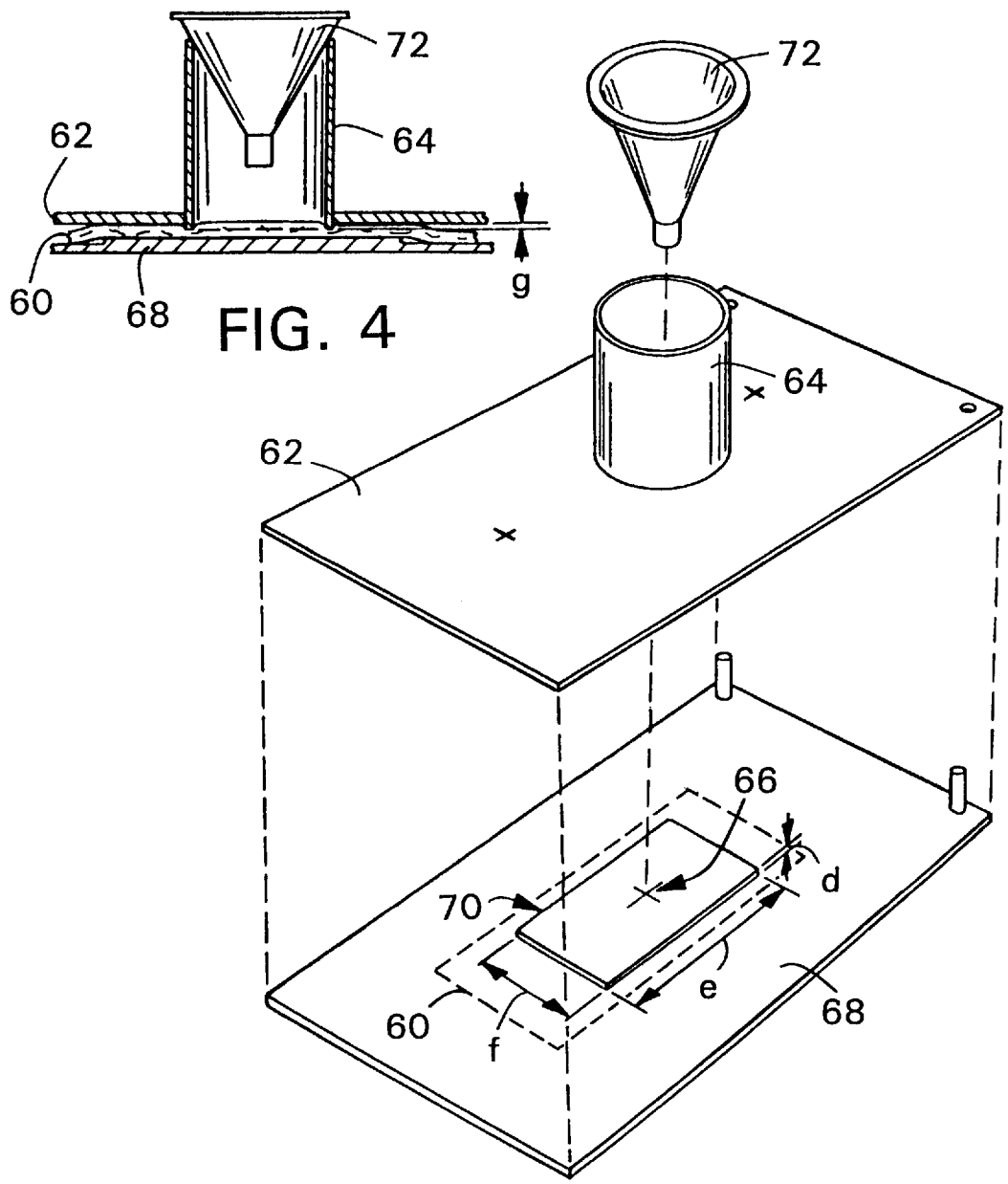
FIG. 3 is an exploded perspective view of a testing apparatus used to conduct the Fluid Intake Evaluation described in connection with the examples.
FIG. 4 is a side elevational view showing the apparatus of FIG. 3 in operation.
Figure 5:
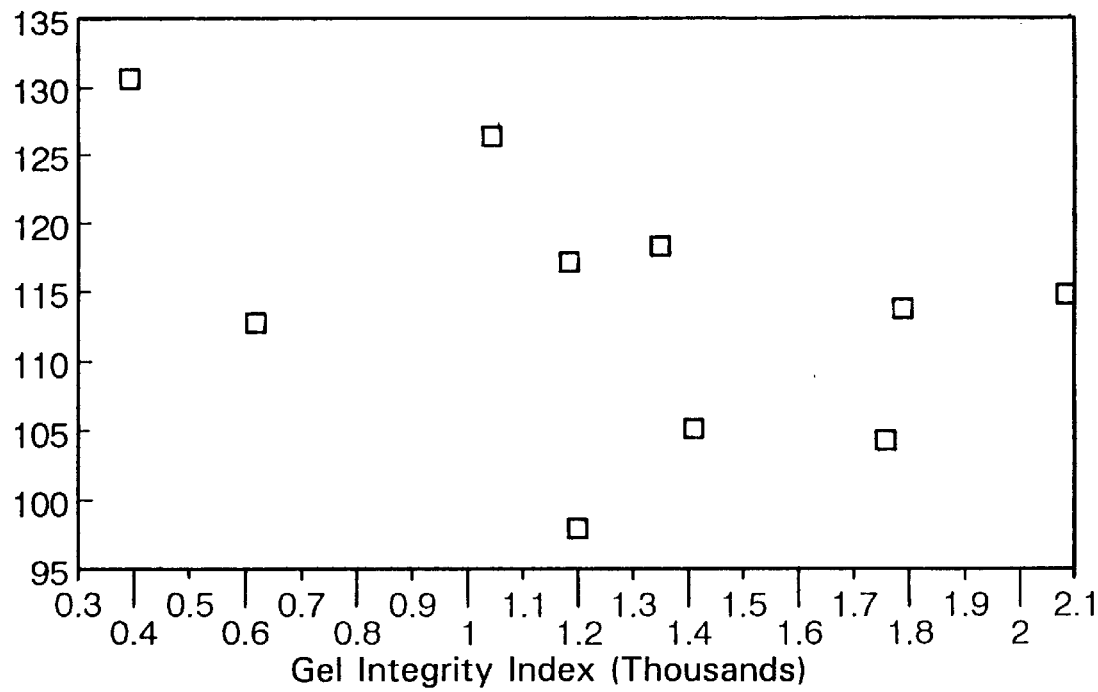
FIGS. 5–14 graphically illustrate the data set forth in Table 3.
Figure 6:
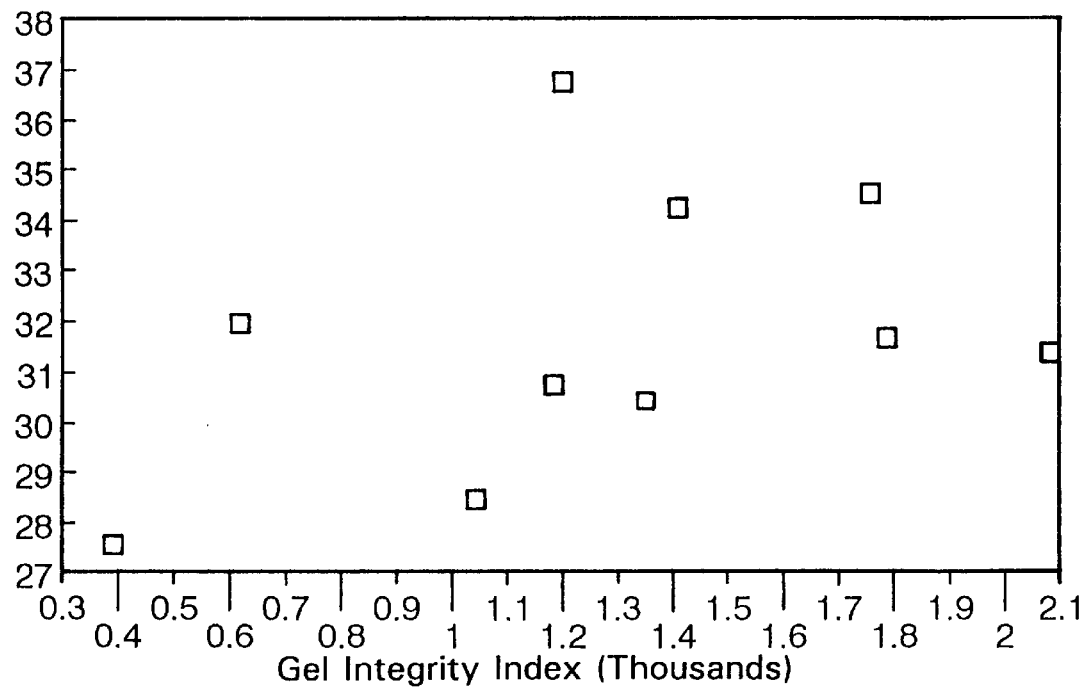
Figure 7:
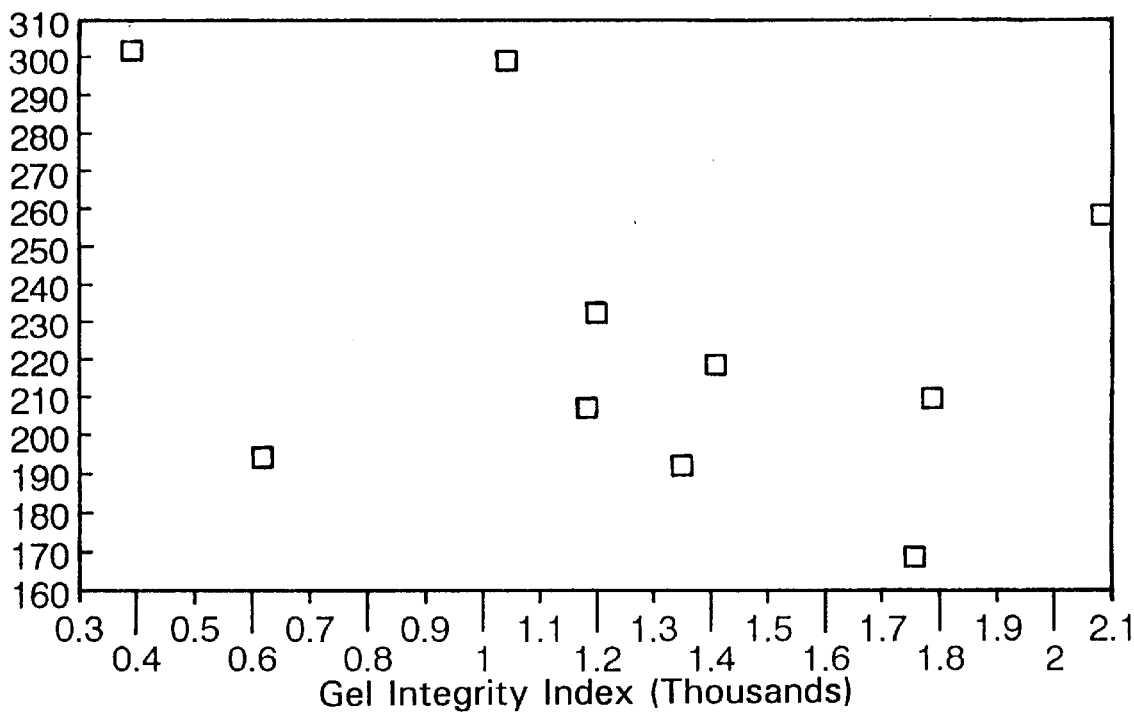
Figure 8:
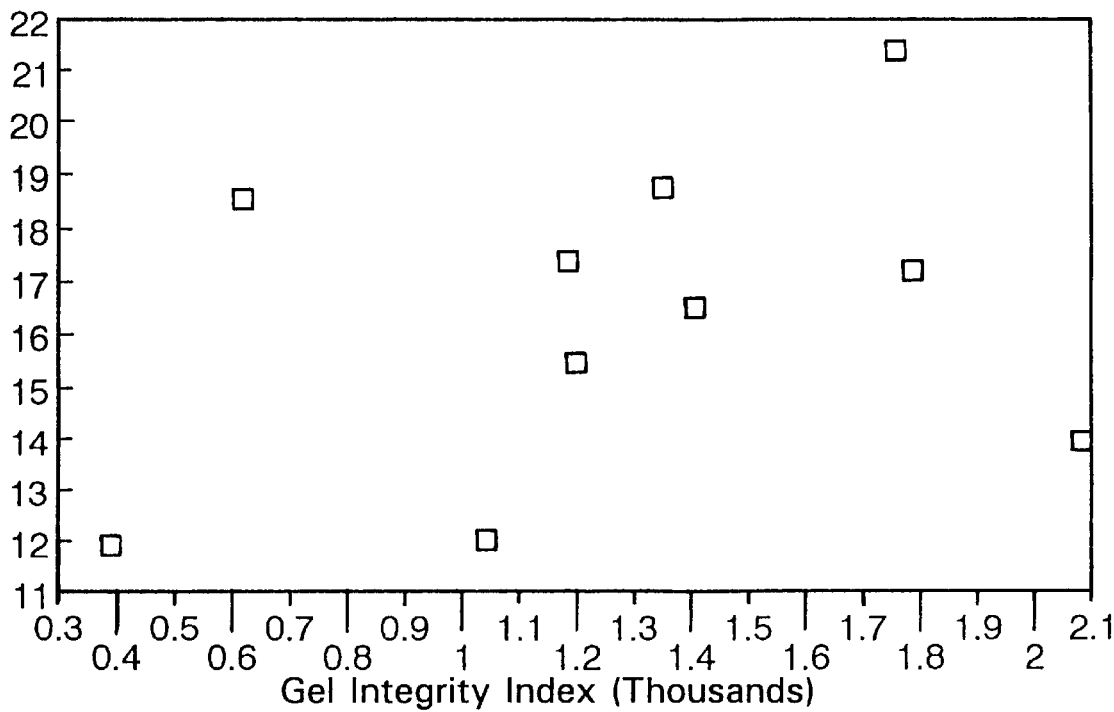
Figure 9:
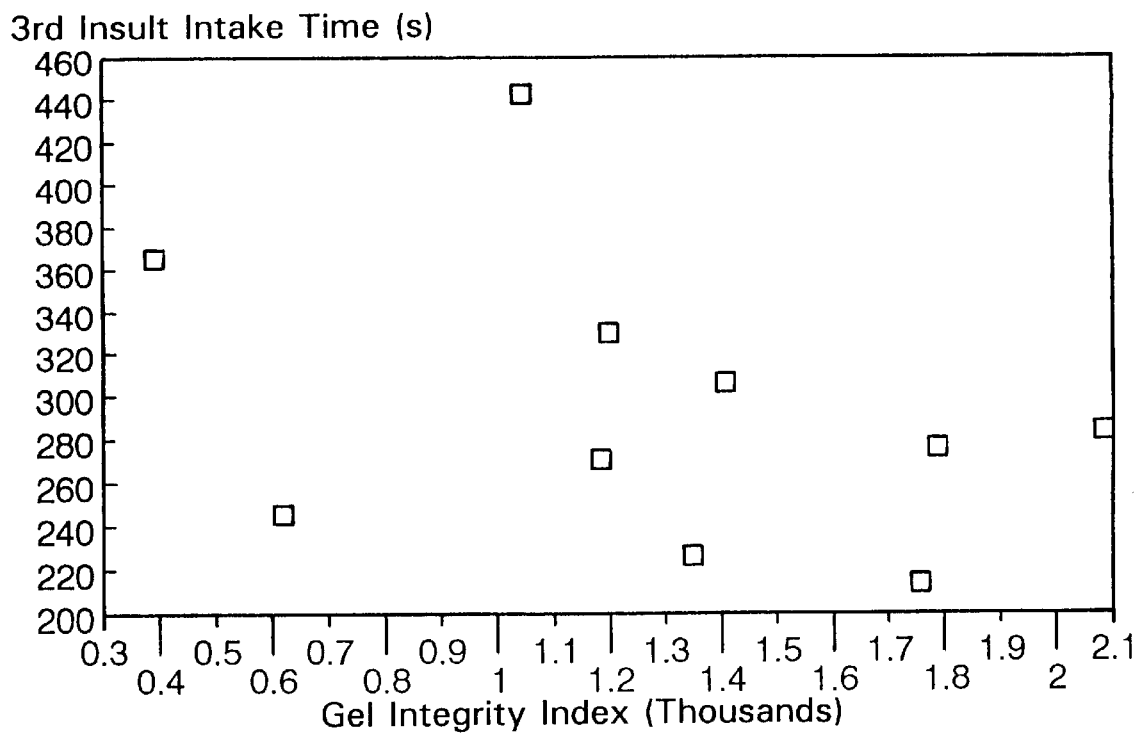
Figure 10:
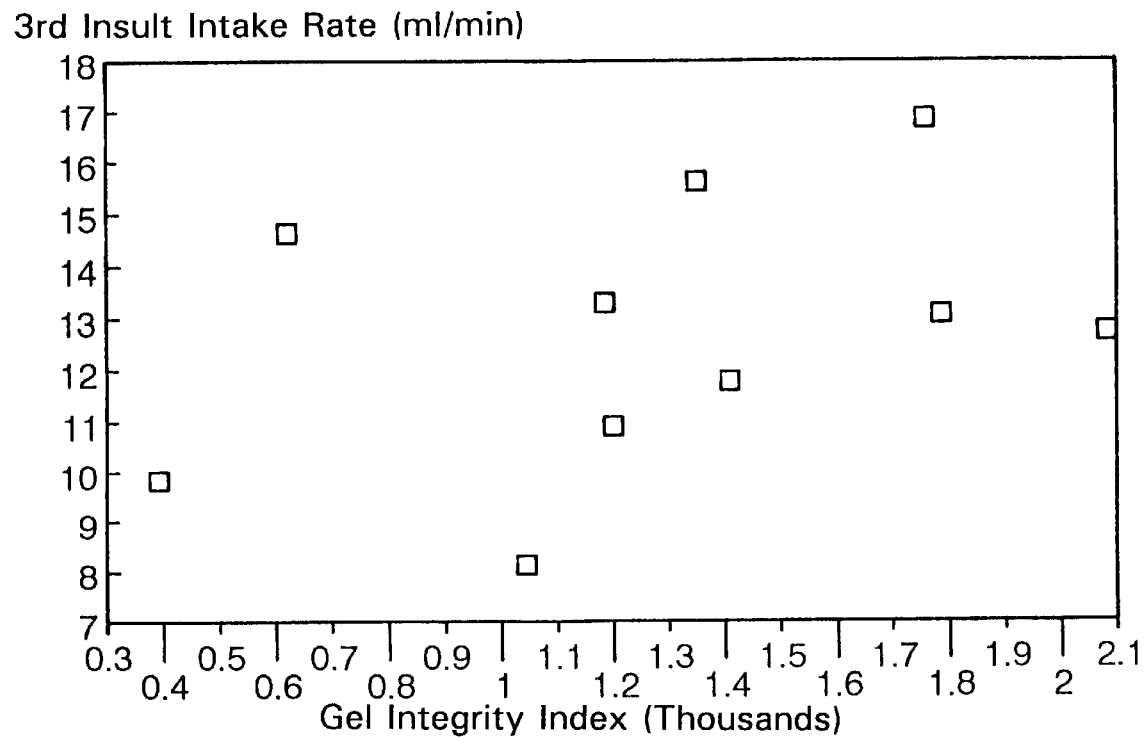
Figure 11:
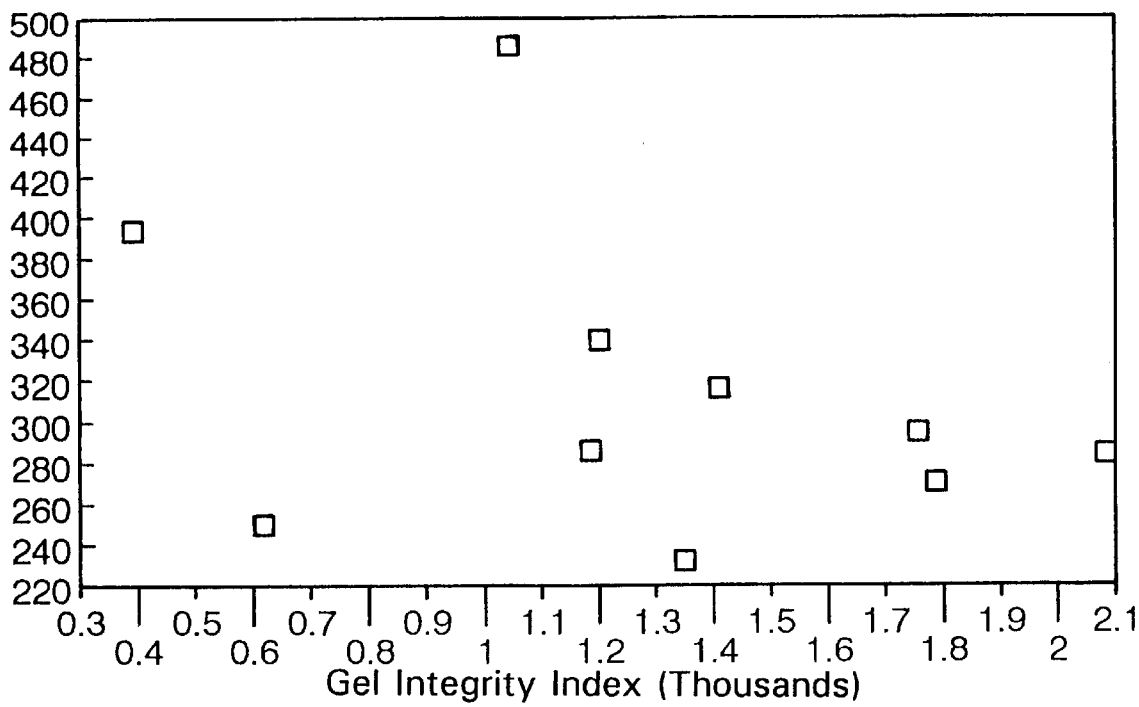
Figure 12:
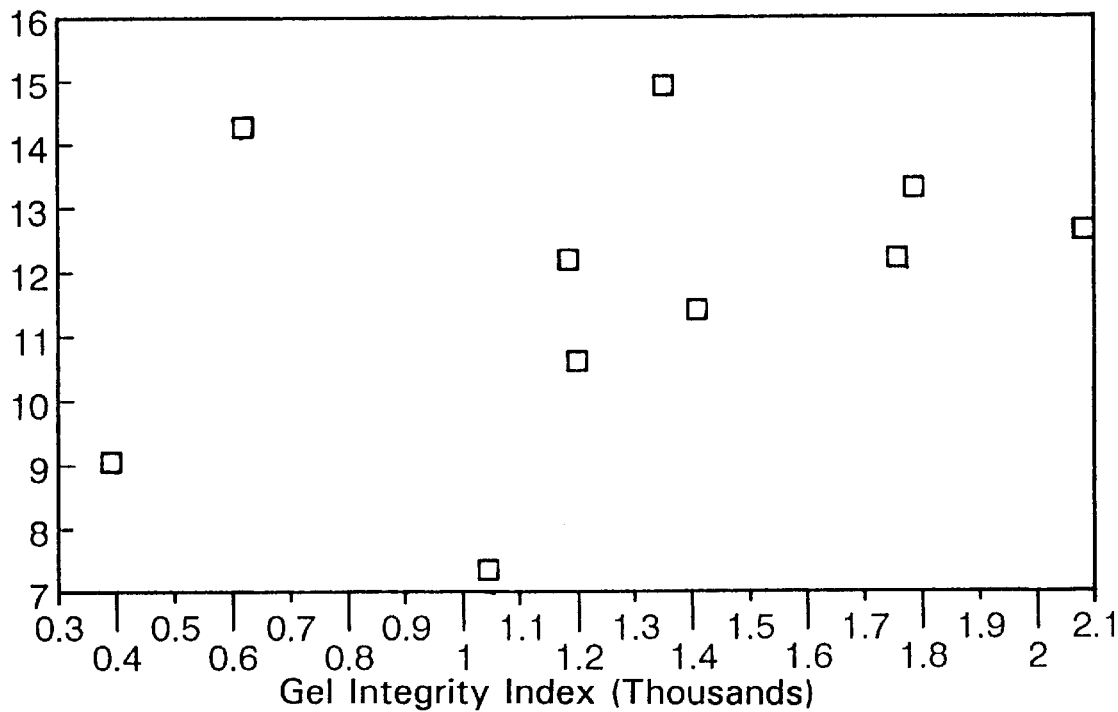
Figure 13:
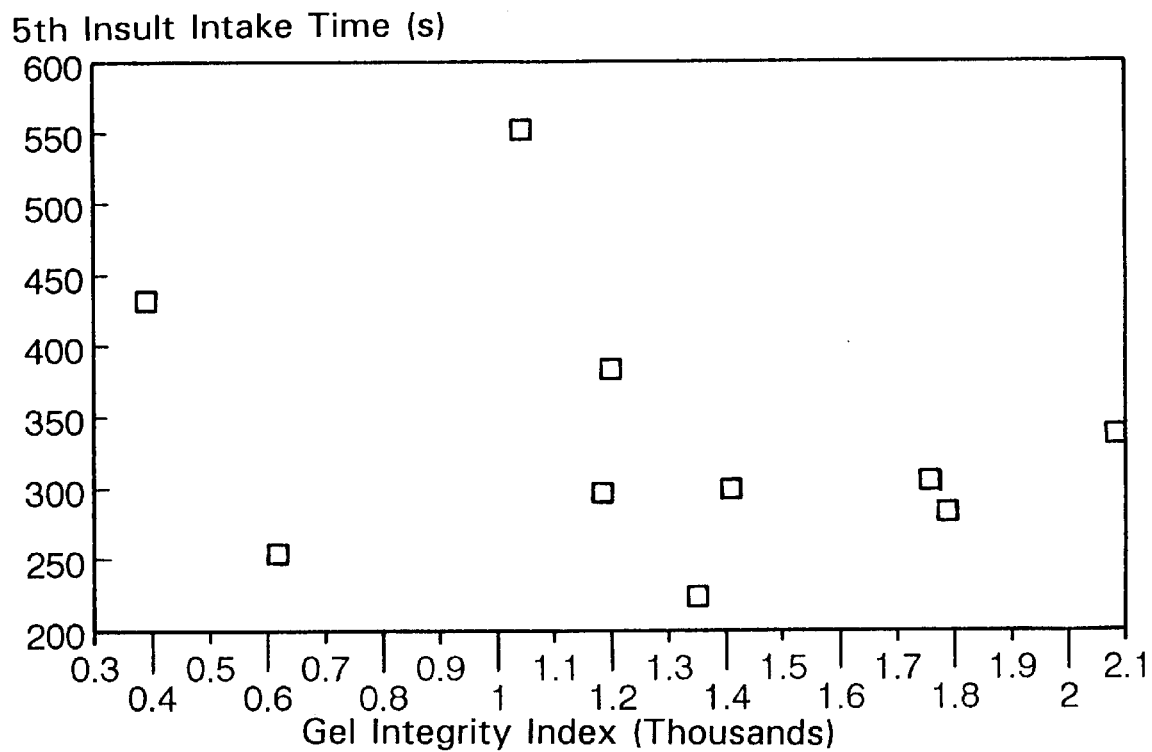
Figure 14:
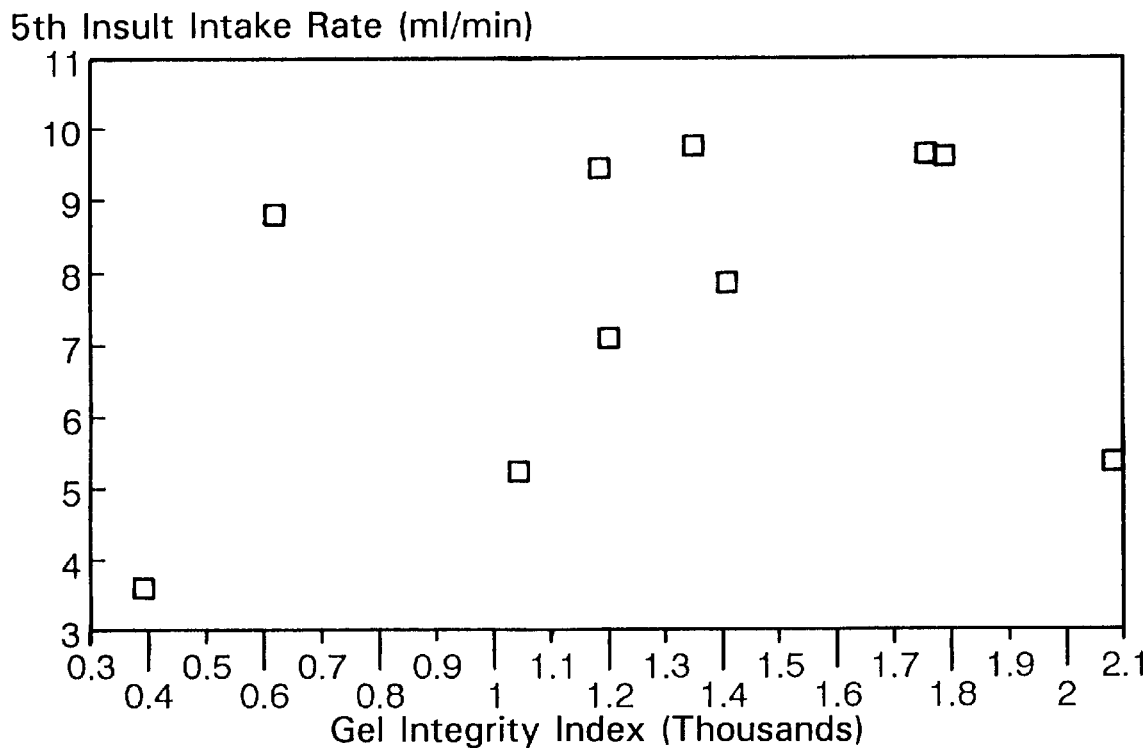

FIGS. 3 and 4 illustrate the test apparatus used to conduct the fluid intake evaluation. With reference to FIG. 3, a 4 inch×10 inch test sample (shown in phantom at 60) is provided. The test sample 60 is placed flat and smooth under a cylinder plate assembly 62 such that the cylinder 64, which has a 5.1 centimeter internal diameter, is positioned over the center 66 of lower plate 68 and raised platform 70. Plate 62 and 68 are 14 inches long and 8 inches wide and are formed from a material such as Plexiglas. Raised platform 70 is ½ inch high (d) by 6 inches long (e) by 3 inches wide (f). The cylinder 64 extends a distance (g) of about 1/32 inch below the cylinder plate assembly 62. This can be seen by reference to FIG. 4. Funnel 72 is sized to fit in cylinder 64 and has a receiving end which is 7 centimeters in diameter and an exit end which is 1.2 centimeters in diameter.

The fluid intake evaluation is performed as follows. The 4 inch by 10 inch test sample 60 is positioned over raised platform 70 such that it is centered thereon. Two 3 inch by 11 inch strips of blotter paper are provided. The blotter paper is 100 pound blotter paper commercially available from James River Corporation under the trade designation 100 pound Verigood Blotter Paper. Each blotter paper strip is weighed and its weight recorded. One strip of blotter paper is placed immediately adjacent, but not touching, each longtudinal side (10 inch) of the test sample 60. Cylinder plate assembly 62 is placed on top of lower plate 68 such that they are superimposed on one another. Two cylindrical weights are placed at the areas marked with an "x" (FIG. 3) so that a 0.836 pound per square inch weight is applied to the 3"×6" portion of test sample 60 located on the raised platform 70, (less the area under cylinder 64). The total weight applied is approximately 12.4 pounds (5623 grams).

Sixty milliliters of a 0.87 percent aqueous saline solution commercially available from Baxter Scientific under the trade designation Blood Bank Saline is poured through funnel 72 in cylinder 64 so as to reach test sample 60. The time required for the 60 milliliter saline solution to disappear from the surface of the test sample 60 is recorded. After the fluid disappears from the surface of the test sample, the blotter strips are removed and weighed to determine the amount of liquid absorbed by the blotter strips. New blotter strips are weighed and placed next to the test sample and a second 60 milliliter insult is applied through the funnel 10 minutes after the first insult was applied. Again, the time required for the fluid to disappear from the surface of the test sample is recorded. The blotter strips are removed and weighed to determine the amount of liquid absorbed by the blotter strips. The procedure of replacing the blotter strips with new strips, insulting the test sample with 60 milliliters of Blood Bank Saline, determining the amount of time necessary for the fluid to disappear from the surface of the test sample 60 and determining the amount of liquid absorbed by the blotter strips is repeated for a total of 5 insults. Each insult occurs 10 minutes after the prior insult. The amount of leakage for each insult is determined by subtracting the dry blotter weights from the wet blotter weights for the blotter strips used for that insult. The intake rate for each insult is determined by subtracting the leakage from the 60 milliliter insult and dividing by the intake time [(60 ml−leakage)/intake time (min)].

EXAMPLES

The following superabsorbent materials were tested. All superabsorbent materials were particulate in form.

TABLE 1

| Sample No. | Manufacturer | Designation |
|---|---|---|
| 1 | Dow Chemical Co. | AFA65-34 |
| 2 | Allied Colloids | DP6-6664 Batch 2 |
| 3 | Allied Colloids | DP6-6664 Batch 4 |
| 4 | Allied Colloids | DP6-6664 Batch 3 |
| 5 | Hoechst Celanese | IM3900 Lot 3175E2 |
| 6 | Allied Colloids | DP6-6664 Batch 1 |
| 7 | Allied Colloids | DP6-6664 Batch 12 |
| 8 | Dow Chemical Co. | Schooner 1 |
| 9 | Dow Chemical Co. | BK 94003 |
| 10 | Stockhausen Inc. | T 5209 |

All of the superabsorbent materials tested were polyacrylic acid superabsorbents. The superabsorbent materials described in Table 1 were tested to determine their gel integrity index. The results of this testing are set forth in Table 2.

TABLE 2

| Sample No. | Gel Integrity Index ($Kg_f \times$ mm) |
|---|---|
| 1 | 2084.3 |
| 2 | 1757.3 |
| 3 | 1350.3 |
| 4 | 1186 |
| 5 | 619.4 |
| 6 | 1788.4 |
| 7 | 1409.1 |
| 8 | 1200.1 |

TABLE 2-continued

| Sample No. | Gel Integrity Index ($Kg_f \times$ mm) |
|---|---|
| 9 | 1044.6 |
| 10 | 392.4 |

The superabsorbent materials described in Table 1 were then formed into absorbent composites. The absorbent composites were formed by air laying a mixture of the superabsorbent material and wood pulp fluff. The wood pulp fluff was a soft wood kraft pulp available from Kimberly-Clark Corporation under the trade designation CR1654. The absorbent composites were air laid so that the superabsorbent material was generally homogeneously distributed within the absorbent composite. The absorbent composites comprised 39 weight percent superabsorbent material based on total weight of the absorbent composite. The absorbent composites had a basis weight of 700 grams per square meter and were densified in a press to have a density of 0.20 gram per cubic centimeter. The absorbent composites, after air laying and densification, were cut to a size of 4 inches×10 inches. The absorbent composites so formed were then subjected to the Fluid Intake Evaluation test described above. The results of this testing are set forth in Table 3 and represent the average of three replications.

TABLE 3

| Superabsorbent Sample No.[1] | 1st Insult | | | 2nd Insult | | | 3rd Insult | | | 4th Insult | | | 5th Insult | | |
|---|---|---|---|---|---|---|---|---|---|---|---|---|---|---|---|
| | Intake[2] | Leakage[3] | Rate[4] | Intake | Leakage | Rate | Intake | Leakage | Rate | Intake | Leakage | Rate | Intake | Leakage | Rate |
| 1 | 114.74 | 0 | 31.38 | 258.28 | 0 | 13.94 | 283.0 | 0 | 12.72 | 283.84 | 0.02 | 12.64 | 336.97 | 29.92 | 5.36 |
| 2 | 104.29 | 0 | 34.52 | 168.29 | 0 | 21.39 | 213.61 | 0 | 16.85 | 294.72 | 0 | 12.21 | 305.07 | 10.97 | 9.64 |
| 3 | 118.33 | 0 | 30.42 | 191.98 | 0 | 18.75 | 226.31 | 1.05 | 15.63 | 231.67 | 2.4 | 14.92 | 224.03 | 23.57 | 9.76 |
| 4 | 117.13 | 0 | 30.74 | 207.1 | 0 | 17.38 | 270.44 | 0.043 | 13.30 | 285.99 | 1.88 | 12.19 | 296.76 | 13.34 | 9.43 |
| 5 | 112.71 | 0 | 31.94 | 194.2 | 0 | 18.54 | 245.85 | 0 | 14.64 | 250.17 | 0.51 | 14.27 | 254.04 | 22.71 | 8.81 |
| 6 | 113.72 | 0 | 31.66 | 209.28 | 0 | 17.20 | 275.45 | 0 | 13.01 | 270.49 | 0 | 13.31 | 283.61 | 14.57 | 9.61 |
| 7 | 105.19 | 0 | 34.22 | 218.35 | 0 | 16.49 | 305.83 | 0 | 11.77 | 315.61 | 0 | 11.41 | 299.16 | 20.83 | 7.86 |
| 8 | 97.95 | 0 | 36.75 | 232.83 | 0 | 15.46 | 330.01 | 0 | 10.91 | 339.2 | 0 | 10.61 | 383.64 | 14.66 | 7.09 |
| 9 | 126.4 | 0 | 28.48 | 299.54 | 0 | 12.02 | 442.95 | 0 | 8.13 | 485.5 | 0.44 | 7.36 | 552.46 | 11.79 | 5.24 |
| 10 | 130.66 | 0 | 27.55 | 302.23 | 0 | 11.91 | 365.69 | 0 | 9.84 | 393.78 | 0.57 | 9.06 | 432.19 | 33.98 | 3.61 |

[1]From Table 1
[2]Intake time in seconds
[3]Leakage in milliliters
[4]Rate in milliliters per minute The data appearing in Table 3 appears in graph form in FIGS. 5–14. As can be seen from reference to Table 3 and FIGS. 9–14, absorbent composites made from superabsorbent materials having a relatively high gel integrity index possess improved intake rates particularly on the third, fourth, and fifth insults. This is important as the third, fourth, and fifth insults tend to simulate in-use situations corresponding to a high level of liquid loading (for example, overnight usage). Thus, while GII does not appear to strongly affect the intake rate of the first insult, the intake rate of second, third, fourth, and fifth insults does, increasingly, appear to be affected by the gel integrity index.

While the invention has been described in detail with respect to specific embodiments thereof, it will be appreciated that those skilled in the art, upon obtaining an understanding of the foregoing, may readily conceive of alterations to, variations of, and equivalents to these embodiments. Accordingly, the scope of the present invention should be assessed as that of the appended claims and any equivalents thereto.

What is claimed is:

1. An absorbent composite for use in a disposable absorbent garment, said absorbent composite comprising:

means for containing a superabsorbent material; and a superabsorbent material contained by said containment means, said superabsorbent material having a Gel Integrity Index, measuring the resistance to penetration of a gel slurry containing the superabsorbent material, of at least about 1500 $Kg_f \times mm$, said superabsorbent being present in said containment means in an amount of from about 10 to about 100 weight percent based on total weight of said containment means and said superabsorbent material;

said Gel Integrity Index being the resistance of a sample of a gel slurry containing the superabsorbent material to the introduction of a test probe into the sample, measured by (1) mixing one part by weight of superabsorbent material having a moisture content of less than 10 weight percent and 50 parts of an aqueous solution containing 0.9 weight percent sodium chloride, in a container having a 33 millimeter diameter and a height of 62 millimeters;

(2) allowing the superabsorbent material to swell for at least one hour until it appears to have generally reached equilibrium; and (3) measuring the resistance of a sample of the mixture of swollen superabsorbent and aqueous solution of sodium chloride to penetration to a test probe, by (a) attaching a clear anodized aluminum test probe having a 1.27 centimeter diameter, a length of 11.43 centimeters, and a rounded end having a 6.35 millimeter radius, to descend downward from a load cell capable of determining the load exerted on the load cell by the test probe;

(b) raising the sample of the mixture of swollen superabsorbent and aqueous solution of sodium chloride to the rounded end of the probe until a load greater than 0.1 gram but less than one gram is exerted on the load cell;

(c) lowering the test probe into the sample, for a distance of 40 millimeters at a constant speed of 16 inches per minute; and (d) determining the resistance of the sample to the introduction of the test probe into the sample, as the probe penetrates from 15 to 40 millimeters into the sample.

2. The absorbent composite according to claim 1 wherein said superabsorbent material is present in said containment means in an amount of from about 30 to about 100 weight percent, based on total weight of said containment means and said superabsorbent material.

3. The absorbent composite according to claim 1 wherein said superabsorbent material is present in said containment means in an amount of from about 50 to about 100 weight percent, based on total weight of said containment means and said superabsorbent material.

4. The absorbent composite according to claim 1 wherein said superabsorbent material is present in said containment means in an amount of from about 30 to about 70 weight percent, based on total weight of said containment means and said superabsorbent material.

5. The absorbent composite according to claim 1 wherein said superabsorbent material has a Gel Integrity Index of at least about 1600 $Kg_f \times mm$.

6. The absorbent composite according to claim 1 wherein said superabsorbent material has a Gel Integrity Index of at least about 1700 $Kg_f \times mm$.

7. The absorbent composite according to claim 1 wherein said superabsorbent material has a Gel Integrity Index of at least about 1900 $Kg_f \times mm$.

8. The absorbent composite according to claim 1 wherein said superabsorbent material has a Gel Integrity Index of at least about 2100 $Kg_f \times mm$.

9. The absorbent composite according to claim 1 wherein said superabsorbent material has a Gel Integrity Index of from about 1500 $Kg_f \times mm$ to about 5000 $Kg_f \times mm$.

10. The absorbent composite according to claim 1 wherein said superabsorbent material has a Gel Integrity Index of from about 1700 $Kg_f \times mm$ to about 4500 $Kg_f \times mm$.

11. The absorbent composite according to claim 1 wherein said superabsorbent material has a Gel Integrity Index of from about 1900 $Kg_f \times mm$ to about 5000 $Kg_f \times mm$.

12. The absorbent composite according to claim 1 wherein said containment means comprises a matrix of fibers.

13. The absorbent composite according to claim 12 wherein said matrix of fibers comprises cellulosic fibers.

14. The absorbent composite according to claim 1 wherein said superabsorbent material is shell crosslinked.

15. The absorbent composite according to claim 1 wherein said containment means comprises two layers of material, at least one layer being water pervious and wherein said superabsorbent material is located between said two layers of material.

16. A disposable garment, said garment comprising:

an outer cover;

a bodyside liner superimposed on said outer cover; and an absorbent composite located between said outer cover and said bodyside lines, said absorbent composite comprising:

means for containing a superabsorbent material; and a superabsorbent material contained by said containment means, said superabsorbent material having a Gel Integrity Index, measuring the resistance to penetration of a gel slurry containing the superabsorbent material, of at least about 1500 $Kg_f \times mm$, said superabsorbent being present in said containment means in an amount of from about 10 to about 100 weight percent based on total weight of said containment means and said superabsorbent material;

said Gel Integrity Index being the resistance of a sample of a gel slurry containing the superabsorbent material to the introduction of a test probe into the sample, measured by (1) mixing one part by weight of superabsorbent material having a moisture content of less than 10 weight percent and 50 parts of an aqueous solution containing 0.9 weight percent sodium chloride, in a container having a 33 millimeter diameter and a height of 62 millimeters;

(2) allowing the superabsorbent material to swell for at least one hour until it appears to have generally reached equilibrium; and (3) measuring the resistance of a sample of the mixture of swollen superabsorbent and aqueous solution of sodium chloride to penetration to a probe, by (a) attaching a clear anodized aluminum test probe having a 1.27 centimeter diameter, a length of 11.43 centimeters, and a rounded end having a 6.35 millimeter radius, to descend downward from a load cell capable of determining the load exerted on the load cell by the test probe;

(b) raising the sample of the mixture of swollen superabsorbent and aqueous solution of sodium chloride to the rounded end of the probe until a load greater than 0.1 gram but less than one gram is exerted on the load cell;

(c) lowering the test probe into the sample, for a distance of 40 millimeters at a constant speed of 16 inches per minute; and (d) determining the resistance of the sample to the introduction of the test probe into the sample, as the probe penetrates from 15 to 40 millimeters into the sample.

17. The disposable absorbent garment according to claim 16 wherein said superabsorbent material is present in said containment means in an amount of from about 30 to about 100 weight percent, based on total weight of said containment means and said superabsorbent material.

18. The disposable absorbent garment according to claim 16 wherein said superabsorbent material is present in said containment means in an amount of from about 50 to about 100 weight percent, based on total weight of said containment means and said superabsorbent material.

19. The disposable absorbent garment according to claim 16 wherein said superabsorbent material is present in said containment means in an amount of from about 30 to about 70 weight percent, based on total weight of said containment means and said superabsorbent material.

20. The disposable absorbent garment according to claim 16 wherein said superabsorbent material has a Gel Integrity Index of at least about 1600 $Kg_f \times mm$.

21. The disposable absorbent garment according to claim 16 wherein said superabsorbent material has a Gel Integrity Index of at least about 1700 $Kg_f \times mm$.

22. The disposable absorbent garment according to claim 16 wherein said superabsorbent material has a Gel Integrity Index of at least about 1900 $Kg_f \times mm$.

23. The disposable absorbent garment according to claim 16 wherein said superabsorbent material has a Gel Integrity Index of at least about 2100 $Kg_f \times mm$.

24. The disposable absorbent garment according to claim 16 wherein said superabsorbent material has a Gel Integrity Index of from about 1500 $Kg_f \times mm$ to about 5000 $Kg_f \times mm$.

25. The disposable absorbent garment according to claim 16 wherein said superabsorbent material has a Gel Integrity Index of from about 1700 $Kg_f \times mm$ to about 4500 $Kg_f \times mm$.

26. The disposable absorbent garment according to claim 16 wherein said superabsorbent material has a Gel Integrity Index of from about 1900 $Kg_f \times mm$ to about 5000 $Kg_f \times mm$.

27. The disposable absorbent garment according to claim 16 wherein said containment means comprises a matrix of fibers.

28. The disposable absorbent garment according to claim 27 wherein said matrix of fibers comprises cellulosic fibers.

29. The disposable absorbent garment according to claim 16 wherein said superabsorbent material is shell crosslinked.

30. The disposable absorbent garment according to claim 16 wherein said containment means comprises two layers of material, at least one layer being water pervious and wherein said superabsorbent material is located between said two layers of material.

31. An absorbent composite suitable for use in a disposable absorbent garment, said absorbent composite comprising:

a fibrous matrix; and a superabsorbent material present in said fibrous matrix, said superabsorbent material having a Gel Integrity Index, measuring the resistance to penetration of a gel slurry containing the superabsorbent material, of at least about 1500 $Kg_f \times mm$, said superabsorbent being present in said fibrous matrix in an amount of from about 10 to about 100 weight percent based on total weight of said fibrous matrix and said superabsorbent material;

said Gel Integrity Index being the resistance of a sample of a gel slurry containing the superabsorbent material to the introduction of a test probe into the sample, measured by (1) mixing one part by weight of superabsorbent material having a moisture content of less than 10 weight percent and 50 parts of an aqueous solution containing 0.9 weight percent sodium chloride, in a container having a 33 millimeter diameter and a height of 62 millimeters;

(2) allowing the superabsorbent material to swell for at least one hour until it appears to have generally reached equilibrium; and (3) measuring the resistance of a sample of the mixture of swollen superabsorbent and aqueous solution of sodium chloride to penetration to a probe, by (a) attaching a clear anodized aluminum test probe having a 1.27 centimeter diameter, a length of 11.43 centimeters, and a rounded end having a 6.35 millimeter radius, to descend downward from a load cell capable of determining the load exerted on the load cell by the test probe;

(b) raising the sample of the mixture of swollen superabsorbent and aqueous solution of sodium chloride to the rounded end of the probe until a load greater than 0.1 gram but less than one gram is exerted on the load cell;

(c) lowering the test probe into the sample, for a distance of 40 millimeters at a constant speed of 16 inches per minute; and (d) determining the resistance of the sample to the introduction of the test probe into the sample, as the probe penetrates from 15 to 40 millimeters into the sample.

32. The absorbent composite according to claim 31 wherein said superabsorbent material is present in said matrix of fibers in an amount of from about 30 to about 70 weight percent, based on total weight of said matrix of fibers and said superabsorbent material.

33. The absorbent composite according to claim 31 wherein said superabsorbent material is present in said matrix of fibers in an amount of from about 50 to about 100 weight percent, based on total weight of said matrix of fibers and said superabsorbent material.

34. The absorbent composite according to claim 31 wherein said superabsorbent material has a Gel Integrity Index of at least about 1600 $Kg_f \times mm$.

35. The absorbent composite according to claim 31 wherein said superabsorbent material has a Gel Integrity Index of at least about 1700 $Kg_f \times mm$.

36. The absorbent composite according to claim 31 wherein said superabsorbent material has a Gel Integrity Index of at least about 1900 $Kg_f \times mm$.

37. The absorbent composite according to claim 31 wherein said superabsorbent material has a Gel Integrity Index of at least about 2100 $Kg_f \times mm$.

38. The absorbent composite according to claim 31 wherein said superabsorbent material has a Gel Integrity Index of from about 1500 $Kg_f \times mm$ to about 5000 $Kg_f \times mm$.

39. The absorbent composite according to claim 31 wherein said superabsorbent material has a Gel Integrity Index of from about 1700 $Kg_f \times mm$ to about 4500 $Kg_f \times mm$.

40. The absorbent composite according to claim 31 wherein said superabsorbent material has a Gel Integrity Index of from about 1900 $Kg_f \times mm$ to about 5000 $Kg_f \times mm$.

41. The absorbent composite according to claim 31 wherein said matrix of fibers comprises cellulosic fibers.

42. The absorbent composite according to claim 31 wherein said superabsorbent material is shell crosslinked.

43. A disposable garment, said garment comprising:
   an outer cover;
   a bodyside liner superimposed on said outer cover; and
   an absorbent composite located between said outer cover and said bodyside lines, said absorbent composite comprising:
      a fibrous matrix; and
      a superabsorbent material present in said fibrous matrix, said superabsorbent material having a Gel Integrity Index, measuring the resistance to penetration of a gel slurry containing the superabsorbent material, of at least about 1500 $Kg_f \times mm$, said superabsorbent being present in said fibrous matrix in an amount of from about 10 to about 100 weight percent based on total weight of said fibrous matrix and said superabsorbent material;
   said Gel Integrity Index being the resistance of a sample of a gel slurry containing the superabsorbent material to the introduction of a test probe into the sample, measured by
      (1) mixing one part by weight of superabsorbent material having a moisture content of less than 10 weight percent and 50 parts of an aqueous solution containing 0.9 weight percent sodium chloride, in a container having a 33 millimeter diameter and a height of 62 millimeters;
      (2) allowing the superabsorbent material to swell for at least one hour until it appears to have generally reached equilibrium; and
      (3) measuring the resistance of a sample of the mixture of swollen superabsorbent and aqueous solution of sodium chloride to penetration to a probe, by
         (a) attaching a clear anodized aluminum test probe having a 1.27 centimeter diameter, a length of 11.43 centimeters, and a rounded end having a 6.35 millimeter radius, to descend downward from a load cell capable of determining the load exerted on the load cell by the test probe;
         (b) raising the sample of the mixture of swollen superabsorbent and aqueous solution of sodium chloride to the rounded end of the probe until a load greater than 0.1 gram but less than one gram is exerted on the load cell;
         (c) lowering the test probe into the sample, for a distance of 40 millimeters at a constant speed of 16 inches per minute; and
         (d) determining the resistance of the sample to the introduction of the test probe into the sample, as the probe penetrates from 15 to 40 millimeters into the sample.

44. The disposable absorbent garment according to claim 43 wherein said superabsorbent material is present in said matrix of fibers in an amount of from about 30 to about 100 weight percent, based on total weight of said matrix of fibers and said superabsorbent material.

45. The disposable absorbent garment according to claim 43 wherein said superabsorbent material is present in said matrix of fibers in an amount of from about 50 to about 100 weight percent, based on total weight of said matrix of fibers and said superabsorbent material.

46. The disposable absorbent garment according to claim 43 wherein said superabsorbent material is present in said matrix of fibers in an amount of from about 30 to about 70 weight percent, based on total weight of said matrix of fibers and said superabsorbent material.

47. The disposable absorbent garment according to claim 43 wherein said superabsorbent material has a Gel Integrity Index of at least about 1600 $Kg_f \times mm$.

48. The disposable absorbent garment according to claim 43 wherein said superabsorbent material has a Gel Integrity Index of at least about 1700 $Kg_f \times mm$.

49. The disposable absorbent garment according to claim 43 wherein said superabsorbent material has a Gel Integrity Index of at least about 1900 $Kg_f \times mm$.

50. The disposable absorbent garment according to claim 43 wherein said superabsorbent material has a Gel Integrity Index of at least about 2100 $Kg_f \times mm$.

51. The disposable absorbent garment according to claim 43 wherein said superabsorbent material has a Gel Integrity Index of from about 1500 $Kg_f \times mm$ to about 5000 $Kg_f \times mm$.

52. The disposable absorbent garment according to claim 43 wherein said superabsorbent material has a Gel Integrity Index of from about 1700 $Kg_f \times mm$ to about 4500 $Kg_f \times mm$.

53. The disposable absorbent garment according to claim 43 wherein said superabsorbent material has a Gel Integrity Index of from about 1900 $Kg_f \times mm$ to about 5000 $Kg_f \times mm$.

54. The disposable absorbent garment according to claim 43 wherein said containment means comprises cellulosic fibers.

55. The disposable absorbent garment according to claim 43 wherein said superabsorbent material is shell crosslinked.

56. The absorbent composite according to claim 1 wherein the superabsorbent is in particulate form; and wherein, in measuring the Gel Integrity Index, the superabsorbent is screened to have a maximum cross-sectional diameter within the range of from about 300 microns to about 600 microns, prior to mixing the superabsorbent with aqueous solution containing 0.9 weight percent sodium chloride.

57. The absorbent composite according to claim 56 wherein the superabsorbent particles have a maximum cross-sectional diameter from about 50 microns to about 1000 microns.

58. The absorbent composite according to claim 1 wherein the superabsorbent is in fibrous form.

59. The absorbent composite according to claim 1 wherein the Gel Integrity Index is measured by a method as set forth in the Test Methods section of the specification.

60. The disposable absorbent garment according to claim 16 wherein the superabsorbent is in particulate form; and wherein, in measuring the Gel Integrity Index, the superabsorbent is screened to have a maximum cross-sectional diameter within the range of from about 300 microns to about 600 microns, prior to mixing the superabsorbent with aqueous solution containing 0.9 weight percent sodium chloride.

61. The disposable absorbent garment according to claim 60 wherein the superabsorbent particles have a maximum cross-sectional diameter from about 50 microns to about 1000 microns.

62. The disposable absorbent garment according to claim 16 wherein the superabsorbent is in fibrous form.

63. The disposable absorbent garment according to claim 16 wherein the Gel Integrity Index is measured by a method as set forth in the Test Methods section of the specification.

64. The absorbent composite according to claim 31 wherein the superabsorbent is in particulate form; and wherein, in measuring the Gel Integrity Index, the superabsorbent is screened to have a maximum cross-sectional diameter within the range of from about 300 microns to about 600 microns, prior to mixing the superabsorbent with aqueous solution containing 0.9 weight percent sodium chloride.

65. The absorbent composite according to claim 64 wherein the superabsorbent particles have a maximum cross-sectional diameter from about 50 microns to about 1000 microns.

66. The absorbent composite according to claim 31 wherein the superabsorbent is in fibrous form.

67. The absorbent composite according to claim 31 wherein the Gel Integrity Index is measured by a method as set forth in the Test Methods section of the specification.

68. The disposable absorbent garment according to claim 43 wherein the superabsorbent is in particulate form; and wherein, in measuring the Gel Integrity Index, the superabsorbent is screened to have a maximum cross-sectional diameter within the range of from about 300 microns to about 600 microns, prior to mixing the superabsorbent with aqueous solution containing 0.9 weight percent sodium chloride.

69. The disposable absorbent garment according to claim 68 wherein the superabsorbent particles have a maximum cross-sectional diameter from about 50 microns to about 1000 microns.

70. The disposable absorbent garment according to claim 43 wherein the superabsorbent is in fibrous form.

71. The disposable absorbent garment according to claim 43 wherein the Gel Integrity Index is measured by a method as set forth in the Test Methods section of the specification.

* * * * *